(12) United States Patent
Joiner et al.

(10) Patent No.: US 9,301,907 B2
(45) Date of Patent: *Apr. 5, 2016

(54) ORAL CARE COMPOSITIONS COMPRISING PEARLESCENT PIGMENTS

(71) Applicant: Conopco Inc., Englewood Cliffs, NJ (US)

(72) Inventors: Andrew Joiner, Bebington (GB); Andrew Philip Parker, Bebington (GB); Carole Jane Philpotts, Bebington (GB)

(73) Assignee: Conopco Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/696,722

(22) Filed: Apr. 27, 2015

(65) Prior Publication Data

US 2015/0224037 A1 Aug. 13, 2015

Related U.S. Application Data

(63) Continuation of application No. 13/991,175, filed as application No. PCT/EP2011/069678 on Nov. 8, 2011, now Pat. No. 9,050,250.

(30) Foreign Application Priority Data

Dec. 8, 2010 (EP) .................................... 10194114

(51) Int. Cl.

| *A61K 8/26* | (2006.01) |
|---|---|
| *A61K 8/73* | (2006.01) |
| *A61K 8/02* | (2006.01) |
| *A61Q 11/00* | (2006.01) |
| *A61K 8/34* | (2006.01) |
| *A61K 8/81* | (2006.01) |
| *A61K 8/86* | (2006.01) |

(52) U.S. Cl.

CPC ................. *A61K 8/26* (2013.01); *A61K 8/0254* (2013.01); *A61K 8/0258* (2013.01); *A61K 8/0266* (2013.01); *A61K 8/345* (2013.01); *A61K 8/73* (2013.01); *A61K 8/733* (2013.01); *A61K 8/8164* (2013.01); *A61K 8/86* (2013.01); *A61Q 11/00* (2013.01); *A61K 2800/412* (2013.01); *A61K 2800/436* (2013.01); *A61K 2800/592* (2013.01); *A61K 2800/621* (2013.01); *A61K 2800/651* (2013.01); *A61K 2800/92* (2013.01)

(58) Field of Classification Search

USPC .......................................................... 424/49

See application file for complete search history.

(56) References Cited

U.S. PATENT DOCUMENTS

| 3,944,661 A | 3/1976 | Colodney et al. |
|---|---|---|
| 2005/0175552 A1 | 8/2005 | Hoic et al. |
| 2005/0287084 A1 | 12/2005 | Ibrahim et al. |
| 2008/0152599 A1 | 6/2008 | Brignoli et al. |

FOREIGN PATENT DOCUMENTS

| CN | 101204358 | 6/2008 |
|---|---|---|
| EP | 1935395 | 6/2008 |
| GB | 2074859 | 11/1981 |
| JP | 7059491 | 6/1995 |
| JP | 11217320 | 8/1999 |

OTHER PUBLICATIONS

Robin Davies, Dentifrices—an update, Med Oral Patol Oral Cir Bucal, Nov. 2010, 976-982, 1:15, Med Oral Petal Oral Bucal.

*Primary Examiner* — Walter Webb

(74) *Attorney, Agent, or Firm* — Greenberg Traurig, LLP

(57) ABSTRACT

The invention provides an oral care composition suitable for delivering a temporary whitening effect to the surface of teeth, the composition comprising: a continuous phase comprising water or polyhydric alcohol or a mixture thereof; a tooth surface whitening agent which is dispersed in the continuous phase, and a deposition aid for the tooth surface whitening agent; characterized in that the tooth surface whitening agent is a pearlescent pigment in an amount of at least 0.1% by weight based on the total weight of the composition, the pearlescent pigment being formed by coating one or more metal oxide layers onto particles of an inorganic substrate.

5 Claims, No Drawings

ORAL CARE COMPOSITIONS COMPRISING PEARLESCENT PIGMENTS

RELATED APPLICATIONS

This application is a Continuation of National Phase Application Ser. No. 13/991,175 filed under 35 U.S.C. 371 of PCT International Application No. PCT/EP2011/069678, filed on Nov. 8, 2011, which claims priority of European Patent Application No. 10194114.4 filed Dec. 8, 2010, the entirety of the applications are hereby incorporated herein by reference for the teachings therein.

FIELD OF THE INVENTION

The present invention is concerned with oral care compositions. More particularly, the present invention is concerned with oral care compositions containing pearlescent pigments.

BACKGROUND OF THE INVENTION

The colour of the teeth is influenced by a combination of their intrinsic colour and the presence of any extrinsic stains that may form on the tooth surface. Extrinsic colour is linked with the adsorption of materials into the acquired pellicle on the surface of enamel, which ultimately cause staining. Factors that influence extrinsic stain formation include poor tooth brushing technique, smoking, dietary intake of coloured foods (e.g. red wine), subject age and the use of certain cationic agents such as chlorhexidine or metal salts like tin and iron.

Consumers have always had a strong desire for white teeth and many individuals are dissatisfied with their current tooth colour. This desire for whiter teeth has given rise to a growing trend in the increased use of tooth whitening products.

Current whitening toothpastes rely on optimised abrasive and chemical components to maximise stain removal and prevention. During brushing, abrasive particles become temporarily trapped between the toothbrush and the stained tooth surface and abrade away the stain. Chemical components may also be used, usually in conjunction with abrasive particles, and include calcium chelators, polymers, surfactants, enzymes and oxidising agents.

EP 1 935 395 describes a novel optical approach to tooth whitening. On brushing with the toothpaste described in this publication, a blue pigment (in particular blue covarine) is deposited onto the tooth surface, where it is able to change the optical effects of the tooth surface, and enhance the measurement and perception of tooth whiteness. This toothpaste is intended to produce a temporary tooth whitening effect that can be reapplied as frequently as desired, as it contains no harsh chemicals, but is not intended to produce any permanent changes to the colour of the teeth.

The present inventors have now found that certain pearlescent pigments can produce superior temporary tooth whitening effects when used in a context similar to that described in EP 1 935 395.

US2005/0175552 and US2005/0287084 describe compositions for imparting whiteness to teeth, which may include various types of pearlescent particle. The compositions described are evaporative solvent-based systems intended for direct application to the teeth by adhesion or painting, after which they dry to form a film.

SUMMARY OF THE INVENTION

The present invention provides an oral care composition suitable for delivering a temporary whitening effect to the surface of teeth, the composition comprising:

a continuous phase comprising water or polyhydric alcohol or a mixture thereof;
a tooth surface whitening agent which is dispersed in the continuous phase, and
a deposition aid for the tooth surface whitening agent; characterised in that the tooth surface whitening agent is a pearlescent pigment in an amount of at least 0.1% by weight based on the total weight of the composition, the pearlescent pigment being formed by coating one or more metal oxide layers onto particles of an inorganic substrate.

DETAILED DESCRIPTION OF THE INVENTION

Tooth Surface Whitening Agent

The composition of the invention comprises a tooth surface whitening agent which is dispersed in the continuous phase of the composition.

The tooth surface whitening agent is a pearlescent pigment which is formed by coating one or more metal oxide layers onto particles of an inorganic substrate.

The term "pearlescent" in the context of the present invention denotes a pigment in the form of particles which each reflect and partially transmit the incident light. The colour effects obtained are associated with the lamellar structure of these particles and are derived from the physical laws of the optics of thin layers.

Suitable inorganic substrates used to form the pearlescent pigment are composed of particles with a thin platelet or flaky morphology. The term "thin platelet or flaky morphology" in the context of the present invention generally means that such particles will have an aspect ratio (lateral diameter to thickness) of at least 5, preferably at least 10, and a mean thickness in the range of 100 to 1000 nm, preferably in the range of 200 to 600 nm.

The inorganic substrates used to form the pearlescent pigment preferably have a fine particle size. The term "fine particle size" in the context of the present invention generally means that the average particle diameter is less than 65 microns, and is most preferably less than 25 microns. The term "diameter" as used herein, means the largest distance across the major axis of the particle. Diameter can be determined by any suitable method known in the art, such as particle size analyzer Mastersizer 2000 manufactured by Malvern Instruments.

Examples of suitable inorganic substrates include natural or synthetic mica flakes (such as muscovite, phlogopite, fluorophlogopite and biotite), other sheet silicates (such as talc, kaolin and sericite), glass platelets, silica flakes, borosilicate flakes and alumina flakes. The substrate need not be totally transparent but should, preferably, have at least about 75% transmission. Natural or synthetic mica flakes are preferred.

The pearlescent pigment is formed by coating one or more metal oxide layers onto the particles of inorganic substrate which are described above.

Examples of suitable metal oxides include $TiO_2$, $Fe_2O_3$, $TiFe_2O_5$, titanium suboxides, $Fe_3O_4$, $Cr_2O_3$, $Al_2O_3$, $SiO_2$, $ZrO_2$, $ZnO$, $SnO_2$, $CoO$, $Co_3O_4$, $VO_2$, $V_2O_3$, $Sn(Sb)O_2$ or mixtures thereof.

Preferred pearlescent pigments for use in the invention include natural or synthetic mica flakes coated with $TiO_2$ and/or $Fe_2O_3$.

The colour of the pearlescent pigment is a function of the thickness of the metal oxide layer. The required thickness for a specific colour may be different for different materials. Preferred pigment colours in the context of the present invention are silver, white, blue and mixtures thereof.

Particularly preferred pearlescent pigments for use in the invention are natural or synthetic mica flakes coated with $TiO_2$, the pigment having a silver-white colour. For $TiO_2$, a layer of 40 nm to 60 nm or a whole number multiple thereof gives a silver-white colour.

The most preferred pearlescent pigments for use in the invention are natural or synthetic mica flakes coated with $TiO_2$, the pigment having a silver-white colour and the pigment having a mean particle diameter (as defined above) which is less than 25 microns, most preferably less than 15 microns. Such materials are commercially available, for example under the tradenames Timiron® and Candurin®, e.g. Timiron® Supersilk MP-1005 (ex Merck) and Candurin® Silver Fine (ex Merck).

Other examples of suitable pearlescent pigments for use in the invention are natural or synthetic mica flakes coated with $TiO_2$ and having a blue or silver-blue colour. For $TiO_2$, a layer of 100 nm to 130 nm or a whole number multiple thereof gives a blue colour. Other absorption colourants can also be precipitated on top of or simultaneously with the $TiO_2$ layer. Examples are blue pigments such as ferric ferrocyanide, cobalt blue and copper phthalocyanine. Such materials are commercially available for example under the tradenames Mearlin®, Colorona® and Dynacolour®, e.g. Mearlin® Sparkle Blue (ex BASF), Colorona® Dark Blue (ex Merck) and Dynacolour® BB9639ZB15C (ex BASF).

Mixtures of any of the above described materials may also be used.

The amount of pearlescent pigment (as defined above) in compositions of the invention is at least 0.1% by weight based on the total weight of the composition. The amount of pearlescent pigment suitably ranges from 0.1 to 5.0%, preferably from 0.1 to 3.0%, more preferably from 0.2 to 2.0% by total weight pearlescent pigment (as defined above) based on the total weight of the composition.

Deposition Aid

The composition of the invention comprises a deposition aid for the tooth surface whitening agent.

The term "deposition aid" in the context of this invention generally means a material which aids deposition of the tooth whitening agent from the continuous phase of the composition onto the surface of teeth during use of the composition. Use of the composition in the context of this invention typically involves application of the composition to the oral cavity, followed by brushing and/or rinsing).

Suitable deposition aids work by having affinity for both the pearlescent pigment (as defined above) and the surface of the teeth.

Preferred deposition aids are able to aid the deposition of the pearlescent pigment onto the teeth such that tooth surface whiteness is enhanced by at least 20% and more preferably by at least 100%, in comparison to the value obtained for teeth treated in an equivalent manner with a control formulation using the same amount of pearlescent pigment in the absence of the deposition aid.

A convenient measure of enhanced tooth surface whiteness is delta b* measured using a chromameter. A negative value of delta b* indicates a yellow to blue colour shift which has been shown to be one of the primary drivers of tooth surface whiteness as perceived by the consumer.

Accordingly, preferred deposition aids are able to aid the deposition of the pearlescent pigment onto the teeth such that the negative value of delta b* is augmented by at least 20% and more preferably by at least 100%, in comparison to the value obtained for teeth treated in an equivalent manner with a control formulation using the same amount of pearlescent pigment in the absence of the deposition aid.

A simple empirical model for establishing the effect of the deposition aid is as follows:

Polished hydroxyapatite discs are first placed in sterile human saliva for 2 hours to allow a pellicle to form. The discs are then rinsed in water and baseline colour measurements made (using, for example, a Minolta chromameter CR300). The discs are then brushed with either (a) a suspension of the pearlescent pigment in water; or (b) a suspension of the pearlescent pigment in water at the same concentration as in (a), together with the deposition aid. The brushing is best performed using a brushing machine. Following rinsing, the colour of the discs is then re-measured and the change in delta b* is recorded for both treatment (a) and treatment (b). From a comparison of these data, the effect of the deposition aid is readily seen.

Suitable deposition aids for use in the invention include polymeric materials.

Polymeric materials for use as deposition aids in the invention may be naturally or synthetically-derived, and may be ionic or nonionic in nature.

Preferably such polymeric materials are high molecular weight. The term "high molecular weight" in this particular context generally means that the polymeric material has a molecular weight of at least 20,000, more preferably at least 50,000 g/mol, most preferably at least 90,000 g/mol. A suitable method to determine the molecular weight of such polymeric materials is gel permeation chromatography against a polyethylene glycol standard.

A preferred class of polymeric material for use as deposition aids in the invention includes high molecular weight polysaccharides having anionic side groups along the polymer main chain.

Specific examples of such materials include gellan gum and carrageenan. The molecular structure of gellan gum is a straight chain based on repeating glucose, rhamnose and glucuronic acid units. Carrageenan is a cell wall hydrocolloid found in certain species of seaweeds belonging to red algae and is composed of repeating units of galactose and 3,6-anhydrogalactose with sulfate esters in varying amount and location depending on the type of carrageenan.

A particularly preferred class of polymeric material for use as deposition aids in the invention includes high molecular weight polyuronates. Polyuronates are typically linear polymers of uronic acid residues. The term "uronic acid residues" as used herein includes uronic acid groups in the form of the free acid or in the form of a derivative thereof, such as a salt, ester or anhydride.

Suitable polyuronates for use as deposition aids in the invention are formed from (1→4)-linked uronic acid residues selected from α-D-galacturonate, α-L-guluronate, β-D-mannuronate, β-D-glucuronate and mixtures thereof.

Preferred polyuronates for use as deposition aids in the invention are pectin and alginates.

Pectin is naturally present in the cell walls of plants and functions as a binding agent. A common source for extracting pectin is citrus peel. Naturally occurring pectin is an integral part of the complex structure which imparts stability to a plant. In this case, the pectin comprising several different types of neutral sugar molecules, which are present in a complex, defined pattern which contains sequences of (1→4)-linked α-D-galacturonate residues which are sandwiched with sequences of neutral sugar molecules such as rhamnose, galactose, arabinose and other sugar types which describe a well-branched structure. When pectin is extracted, a large part of the branched structure usually disappears and a relatively straight chain, the majority of which consists of (1→4)-linked α-D-galacturonate residues, remains.

Extracted pectin usually contains more than 65% α-D-galacturonate residues. The α-D-galacturonate residues may generally be in the form of the free acid, or the salt of the free acid, or the methyl ester of the free acid. When more than 50% of the α-D-galacturonate residues are in methyl ester form, the pectin is then classified as being high-methyl ester pectin, and when less than 50% of the α-D-galacturonate residues are in methyl ester form it is consequently classified as being low-methyl ester pectin. Some pectins are treated during manufacture with ammonia to produce amidated pectins, in which some of the α-D-galacturonate residues are converted to carboxylic acid amide groups.

Preferred examples of suitable pectins for use in the invention are low-methyl ester pectins. Such materials may be amidated (commercially available under the tradename GENU® Pectin X-916-02, ex CP Kelco) or, more preferably, non-amidated (commercially available under the tradename GENU® Pectin LM-18, ex CP Kelco).

Alginates are a particularly preferred class of polyuronate for use as deposition aids in the invention. "Alginate" is the general name for alginic acid and its salts. Alginates are polysaccharides which may be isolated from brown algae such as *Laminaria hyperborea* and *lessonia* found in coastal waters, and may be characterised as linear copolymers which contain sequences of (1→4)-linked β-D-mannuronate (M) and α-L-guluronate (G) residues, respectively. Naturally occurring alginate has a block-like structure in which stretches of poly-α-L-guluronate are interspersed by stretches of poly-β-D-mannuronate, and by heteropolymeric regions in which both residues occur in arrangements which can range from almost statistically random to almost regularly alternating. The number ratio of mannuronate to guluronate residues is known as the M:G ratio and can vary according to the nature or growth conditions of the source material.

Sodium alginate is the most preferred alginate for use as a deposition aid in the invention. The sodium alginate may for example be of the "high mannuronic" type, characterised by an M:G ratio of at least 1:1, generally at least 1.5:1. Such materials are commercially available, for example under the tradename MANUCOL® DH (ex FMC BioPolymer). Alternatively, and in some cases preferably, the sodium alginate may be of the "high guluronic" type, characterised by an M:G ratio of from 0.1:1 to less than 1:1, generally from 0.2:1 to 0.8:1. Such materials are commercially available, for example under the tradename MANUGEL® GMB (ex FMC BioPolymer).

Mixtures of any of the above described materials may also be used.

The amount of deposition aid (as defined above) in compositions of the invention suitably ranges from 0.01 to 5.0%, preferably from 0.1 to 3.0%, more preferably from 0.2 to 2.0% by total weight deposition aid (as defined above) based on the total weight of the composition.

Product Form

The composition of the invention comprises a continuous phase comprising water or polyhydric alcohol or a mixture thereof.

Examples of suitable product forms for compositions of the invention include dentifrices, mouthwashes, chewing gums and lozenges.

Preferred product forms for compositions of the invention are those which are suitable for brushing and/or rinsing the surfaces of the oral cavity.

In such preferred product forms, the amount of water and/or polyhydric alcohol will generally be at least 10%, preferably at least 30%, more preferably at least 50% by total weight water and/or polyhydric alcohol based on the total weight of the composition.

An example of a preferred type of product form in the context of the present invention is a dentifrice. The term "dentifrice" generally denotes formulations which are used to clean the surfaces of the oral cavity. The dentifrice is an oral composition that is not intentionally swallowed for purposes of systemic administration of therapeutic agents, but is applied to the oral cavity, used to treat the oral cavity and then expectorated. Typically the dentifrice is used in conjunction with a cleaning implement such as a toothbrush, usually by applying it to the bristles of the toothbrush and then brushing the accessible surfaces of the oral cavity. Preferably the dentifrice is in the form of a paste or a gel (or a combination thereof).

A dentifrice composition according to the invention will usually contain a liquid continuous phase in an amount of from 40 to 99% by weight based on the total weight of the dentifrice. Such a liquid continuous phase will typically comprise a mixture of water and polyhydric alcohol in various relative amounts, with the amount of water generally ranging from 10 to 45% by weight (based on the total weight of the dentifrice) and the amount of polyhydric alcohol generally ranging from 30 to 70% by weight (based on the total weight of the dentifrice). Typical polyhydric alcohols include humectants such as glycerol, sorbitol, polyethylene glycol, polypropylene glycol, propylene glycol, xylitol (and other edible polyhydric alcohols), hydrogenated partially hydrolyzed polysaccharides and mixtures thereof.

A dentifrice composition according to the invention will generally contain further ingredients to enhance performance and/or consumer acceptability such as abrasive cleaning agent, binder or thickening agent, and surfactant.

For example, a dentifrice will usually comprise an abrasive cleaning agent in an amount of from 3 to 75% by weight based on the total weight of the dentifrice. Suitable abrasive cleaning agents include silica xerogels, hydrogels and aerogels and precipitated particulate silicas; calcium carbonate, dicalcium phosphate, tricalcium phosphate, calcined alumina, sodium and potassium metaphosphate, sodium and potassium pyrophosphates, sodium trimetaphosphate, sodium hexametaphosphate, particulate hydroxyapatite and mixtures thereof.

Furthermore, the dentifrice will usually contain a binder or thickening agent in an amount of from 0.5 to 10% by weight based on the total weight of the dentifrice. Suitable binders or thickening agents include carboxyvinyl polymers (such as polyacrylic acids cross-linked with polyallyl sucrose or polyallyl pentaerythritol), hydroxyethyl cellulose, hydroxypropyl cellulose, water soluble salts of cellulose ethers (such as sodium carboxymethyl cellulose and sodium carboxymethyl hydroxyethyl cellulose), natural gums (such as carrageenan, gum karaya, guar gum, xanthan gum, gum arabic, and gum tragacanth), finely divided silicas, hectorites, colloidal magnesium aluminium silicates and mixtures thereof.

Furthermore, the dentifrice will usually contain a surfactant in an amount of from 0.2 to 5% by weight based on the total weight of the dentifrice. Suitable surfactants include anionic surfactants, such as the sodium, magnesium, ammonium or ethanolamine salts of $C_8$ to $C_{18}$ alkyl sulphates (for example sodium lauryl sulphate), $C_8$ to $C_{18}$ alkyl sulphosuccinates (for example dioctyl sodium sulphosuccinate), $C_8$ to $C_{18}$ alkyl sulphoacetates (such as sodium lauryl sulphoacetate), $C_8$ to $C_{18}$ alkyl sarcosinates (such as sodium lauryl sarcosinate), $C_8$ to $C_{18}$ alkyl phosphates (which can optionally comprise up to 10 ethylene oxide and/or propylene oxide units) and sulphated monoglycerides. Other suitable surfactants include nonionic surfactants, such as optionally polyethoxylated fatty acid sorbitan esters, ethoxylated fatty acids, esters of polyethylene glycol, ethoxylates of fatty acid monoglycerides and diglycerides, and ethylene oxide/propylene oxide block polymers. Other suitable surfactants include amphoteric surfactants, such as betaines or sulphobetaines. Mixtures of any of the above described materials may also be used.

Another example of a preferred type of product form in the context of the present invention is a mouthwash. The term "mouthwash" generally denotes liquid formulations which are used to rinse the surfaces of the oral cavity and provide the user with a sensation of oral cleanliness and refreshment The mouthwash is an oral composition that is not intentionally swallowed for purposes of systemic administration of therapeutic agents, but is applied to the oral cavity, used to treat the oral cavity and then expectorated.

A mouthwash composition according to the invention will usually contain an aqueous continuous phase. The amount of water generally ranges from 70 to 99% by weight based on the total weight of the mouthwash.

A mouthwash composition according to the invention will generally contain further ingredients to enhance performance and/or consumer acceptability, such as the humectants and surfactants mentioned above for dentifrices. The amount of humectant generally ranges from 5 to 20% by weight based on the total weight of the mouthwash and the amount of surfactant generally ranges from 0.1 to 5% by weight based on the total weight of the mouthwash.

Compositions of the present invention (such as in particular dentifrices or mouthwashes) may also contain further optional ingredients customary in the art such as fluoride ion sources, anticalculus agents, buffers, flavouring agents, sweetening agents, colouring agents, opacifying agents, preservatives, antisensitivity agents and antimicrobial agents.

The invention is further illustrated with reference to the following, non-limiting Examples.

EXAMPLES

Experimental Method

Extracted human anterior teeth were cleaned and the roots mounted in perspex blocks. Any remaining exposed dentine was coated in nail varnish. The teeth were allowed to fully hydrate in deionised water for several days before immersion in whole human saliva for 2 hours to form a pellicle.

The baseline colour of the teeth was measured with a colorimeter in the CIELAB mode. The teeth were then randomly allocated to their respective treatment groups (n=8) which typically consisted of an aqueous mixture of 1% w/w pearlescent pigment (as defined above) plus 1% w/w deposition aid (as defined above).

Controls included a system which is representative of the preferred pigment & deposition aid combination according to EP 1 935 395 (i.e. 0.025% w/w Blue Covarine pigment plus 0.1% w/w GANTREZ®S97 deposition aid ex ISP); and a system without deposition aid (i.e. pearlescent pigment alone).

The treatment time was 1 minute, followed by extensive water rinse.

The colour of the teeth was again measured and changes in CIELAB calculated as Delta L*, Delta a* and Delta b*. For "blue" coloured micas, reduction in b* (i.e. tooth yellowness) was the main parameter for efficacy. For "white" or "silver-white" coloured micas, increase in L* (brightness) was also considered.

Experiment 1

Blue Micas Plus Deposition Polymer

| Example | Treatment | Delta b* (s.d.) |
| --- | --- | --- |
| Comparative Example A | Colorona ® Dark Blue Mica | −1.23 (0.44) |
| Example 1 | Colorona ® Dark Blue Mica + MANUCOL ® DH | −12.51 (2.46) |
| Example 2 | Dynacolour ® Blue Mica + MANUCOL ® DH | −10.87 (2.12) |
| Example 3 | Mearlin ® Sparkle Blue + MANUCOL ® DH | −3.26 (1.21) |
| Comparative Example B | Blue Covarine + GANTREZ ®S97 | −1.62 (0.54) |

This series of results shows that Examples 1 to 3 according to the invention provide superior reduction in tooth yellowness when compared to a system without deposition aid (Comparative Example A) or when compared to a system which is representative of the preferred pigment & deposition aid combination according to EP 1 935 395 (Comparative Example B).

Experiment 2

White/Silver-White Micas Plus Deposition Polymer

| Example | Treatment | Delta L* (s.d.) | Delta b* (s.d.) |
| --- | --- | --- | --- |
| Comparative Example C | Timiron ® Supersilk MP-1005 | 0.17 (0.98) | −0.33 (0.36) |
| Example 4 | Timiron ® Supersilk MP-1005 + 0.5% MANUCOL ® DH | 4.12 (1.69) | −3.01 (1.56) |
| Example 5 | Timiron ® Supersilk MP-1005 + 1.0% MANUCOL ® DH | 7.51 (2.28) | −4.36 (1.80) |
| Example 6 | Timiron ® Supersilk MP-1005 + 1.0% GENU ® Pectin X-916-02 | 2.15 (0.94) | −1.49 (0.61) |
| Example 7 | Candurin ® Silver Fine + 1.0% MANUCOL ® DH | 5.93 (2.10) | −3.05 (1.31) |
| Example 8 | Timiron ® Pearl Sheen + 1.0% MANUCOL ® DH | 4.19 (1.68) | −3.04 (0.67) |
| Comparative Example B | Blue Covarine + GANTREZ ®S97 | −1.13 (0.40) | −1.62 (0.54) |

This series of results shows that Examples 4 to 8 according to the invention provide superior reduction in tooth yellowness and increase in tooth brightness, when compared to a system without deposition aid (Comparative Example C) or when compared to a system which is representative of the preferred pigment & deposition aid combination according to EP 1 935 395 (Comparative Example B).

Experiment 3

Comparison of Deposition Polymers

| Example | Treatment | Delta L* (s.d.) | Delta b* (s.d.) |
|---|---|---|---|
| Example 7 | Candurin ® Silver Fine + 1% MANUCOL ® DH | 5.93 (2.10) | 3.05 (1.31) |
| Example 9 | Candurin ® Silver Fine + 1% GANTREZ ® S97 | 0.91 (0.67) | −0.85 (0.51) |
| Example 10 | Candurin ® Silver Fine + 2% PEG 32 | 0.92 (0.43) | −0.50 (0.95) |

This series of results shows that MANUCOL® DH is an especially effective deposition aid for pearlescent pigments such as Candurin® Silver Fine.

Experiment 4

Mouthwash Formulations

Mouthwash formulations were prepared having ingredients as shown in the following Table:

| Ingredient | Example 11 | Example 12 | Example 13 | Example 14 | Comp. Ex. D |
|---|---|---|---|---|---|
| | (wt %) | | | | |
| Water | 82.26 | 82.26 | 82.26 | 82.26 | 82.26 |
| Sorbitol (70%) | 12.0 | 12.0 | 12.0 | 12.0 | 12.0 |
| PEG40 hydrogenated castor oil | 2.5 | 2.5 | 2.5 | 2.5 | 2.5 |
| Sodium lauryl sulphate | 0.34 | 0.34 | 0.34 | 0.34 | 0.34 |
| Phenoxyethanol | 0.3 | 0.3 | 0.3 | 0.3 | 0.3 |
| Benzyl alcohol | 0.3 | 0.3 | 0.3 | 0.3 | 0.3 |
| Flavour | 0.3 | 0.3 | 0.3 | 0.3 | 0.3 |
| Mica[1] | 1.0 | 1.0 | 1.0 | 1.0 | 1.0 |
| MANUCOL ® DH[2] | 1.0 | — | — | — | — |
| MANUGEL ® GMB[3] | — | 1.0 | — | — | — |
| GENU ® Pectin X-916-02[4] | — | — | 1.0 | — | — |
| GENU ® Pectin LM-18[5] | — | — | — | 1.0 | — |

[1] TIMIRON ® Supersilk MP-1005 (ex Merck), white mica with a particle size of c. 6 microns.
[2] Sodium alginate, high mannuronic acid content, ex FMC Biopolymer
[3] Sodium aginate, high guluronic acid content, ex FMC Biopolymer
[3] Amidated low methoxy pectin, ex CP Kelco
[4] Non-amidated low methoxy pectin, ex CP Kelco The mouthwash samples were tested on extracted molar teeth mounted in plastic. Prior to use, the teeth were immersed in gamma-irradiated human saliva for 24 hours to generate a pellicle layer. Each mouthwash was tested on 6 randomly selected teeth.

The colour of each tooth was measured using a Minolta CR321 Chroma Meter (45° illumination, 0° viewing angle, 3 mm diameter measuring area). Six readings were taken from the front face of the tooth to provide an average colour. Two teeth were then immersed in the mouthwash solution which was being continuously stirred on a magnetic stirrer. After 60 seconds the teeth were removed, excess solution removed by shaking and the colour remeasured. The teeth were then gently agitated in 24° F.H water for 10 seconds and measured again.

Results

| Example | Delta L* (s.d.) post-treatment | Delta b* (s.d.) post-treatment | Delta L* (s.d.) post-rinse | Delta b* (s.d.) post-rinse |
|---|---|---|---|---|
| Comp. Ex. D | 1.389 (0.395) | −0.940 (0.283) | 0.342 (0.076) | −0.437 (0.510) |
| Example 11 | 2.668 (1.015) | −2.042 (1.085) | −0.098 (0.380) | −0.300 (0.289) |
| Example 12 | 4.159 (0.447) | −2.932 (1.008) | 0.768 (0.426) | −0.566 (0.662) |
| Example 13 | 2.474 (1.073) | −1.681 (0.459) | 0.264 (0.264) | −0.404 (0.270) |
| Example 14 | 5.142 (1.584) | −3.028 (1.347) | 4.144 (1.786) | −2.996 (1.207) |

The whiteness benefit is obtained in two ways, by increasing the lightness (L*) value and/or by decreasing the b* (which counters the natural yellowness of the teeth).

This series of results shows that post-treatment, Examples 11 to 14 according to the invention provide superior increase in L*, when compared to a system without deposition aid (Comparative Example D). Examples 11, 12 and 14 provide significant increases in L*. Examples 12 and 14 also provide significant decreases in b*, relative to the Comparative Example. Example 14 also provides improved results post-rinsing, implying greater post-rinse retention of this system on the teeth.

We claim:

1. An oral care composition comprising:
   a continuous phase comprising at least one of water, polyhydric alcohol or a mixture thereof;
   a tooth surface whitening agent which is dispersed in the continuous phase, and
   a deposition aid for the tooth surface whitening agent;
   wherein the tooth surface whitening agent comprises a pearlescent pigment in an amount of from 1 to 5% by weight based on the total weight of the oral care composition;
   wherein the pearlescent pigment comprises particles of an inorganic substrate;
   wherein the particles have a coating of one or more metal oxide layers;
   and wherein the deposition aid is sodium alginate having a molecular weight of at least 20,000 g/mol.

2. The oral care composition according to claim 1, wherein the particles of the pearlescent pigment are selected from at least one of natural or synthetic mica flakes coated with at least one of $TiO_2$ or $Fe_2O_3$.

3. The oral care composition according to claim 1, which is in the form of a dentifrice or a mouthwash.

4. The oral care composition according to claim 1, wherein the deposition aid is present in an amount of 0.01 to 5% by weight based on the total weight of the oral care composition.

5. An oral care composition comprising:
   a continuous phase comprising at least one of water, polyhydric alcohol or a mixture thereof;
   a tooth surface whitening agent which is dispersed in the continuous phase, and
   a deposition aid for the tooth surface whitening agent;
   wherein the tooth surface whitening agent comprises a pearlescent pigment in an amount of from 0.2 to 2% by weight based on the total weight of the oral care composition, wherein the pearlescent pigment comprises particles of an inorganic substrate,
   wherein the particles have a coating of one or more metal oxide layers; and wherein the deposition aid is a sodium alginate having a molecular weight of at least 20,000 g/mol.

* * * * *